United States Patent [19]

Dorn et al.

[11] 4,164,449

[45] Aug. 14, 1979

[54] SURFACE SEPARATION TECHNIQUE FOR THE DETECTION OF MICROBIAL PATHOGENS

[75] Inventors: Gordon L. Dorn, Dallas, Tex.; John R. Haynes, Florissant, Mo.

[73] Assignee: J. K. and Susie L. Wadley Research Institute and Blood Bank, Dallas, Tex.

[21] Appl. No.: 848,337

[22] Filed: Nov. 3, 1977

[51] Int. Cl.² ............................................. C12K 1/04
[52] U.S. Cl. ................................................... 435/30
[58] Field of Search ................................. 195/103.5 M

[56] References Cited

U.S. PATENT DOCUMENTS 3,928,139  12/1975  Dorn ........................... 195/103.5 M

*Primary Examiner*—Raymond N. Jones
*Assistant Examiner*—Robert J. Warden
*Attorney, Agent, or Firm*—Richards, Harris & Medlock

[57] ABSTRACT

A method for concentrating and separating microbial pathogens present in a blood sample is provided. Initially, a blood sample is injected into a closed evacuated space within an elongated centrifugation receptacle which comprises a smooth continuous surface at one end thereof. The centrifugation article is then subjected to centrifugation causing any microbial pathogens present in the blood sample to move toward the end of the elongated centrifugation receptacle which comprises the smooth continuous surface and collect thereon. After centrifugation, the major portion of the residual blood sample is removed from the centrifugation receptacle and the separated and concentrated microbial pathogens can then be removed for quantitative and qualitative analysis.

10 Claims, 9 Drawing Figures

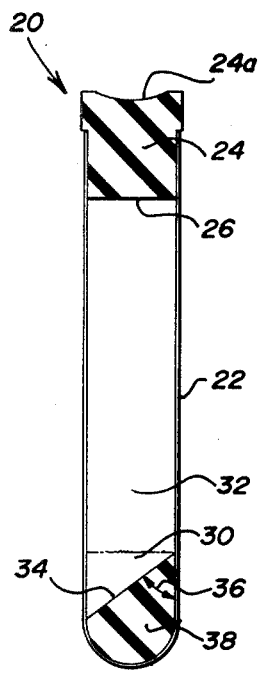
FIG. 1
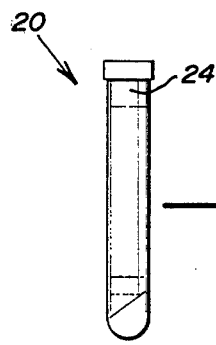
FIG. 2
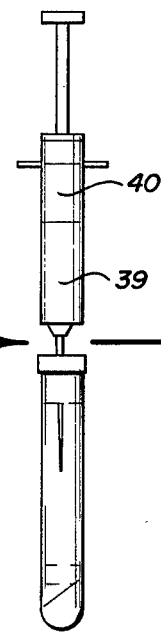
FIG. 3
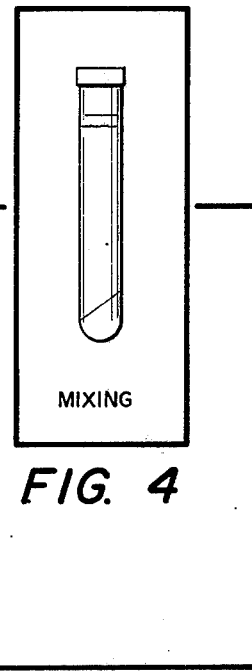
FIG. 4
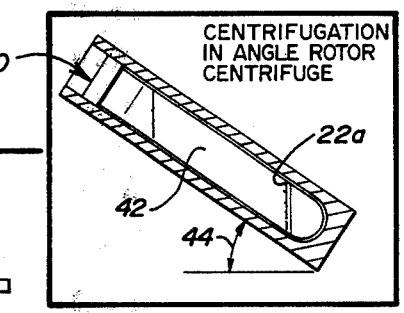
FIG. 5
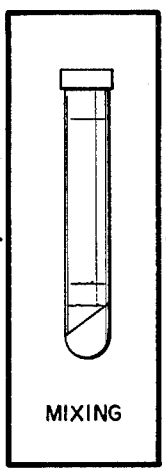
FIG. 6
FIG. 7
FIG. 8
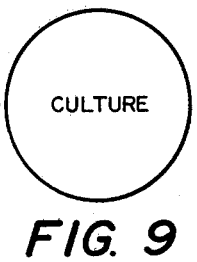
FIG. 9

SURFACE SEPARATION TECHNIQUE FOR THE DETECTION OF MICROBIAL PATHOGENS

BACKGROUND OF THE INVENTION

This invention relates to a novel method for detecting the presence of microbial pathogens in a blood sample. In another aspect, this invention provides a novel technique for selectively separating and concentrating microbial pathogens from a blood sample. In still another aspect, this invention relates to a method for separating microbial pathogens from a lysed blood sample which may contain other components, such as antimicrobial constituents of blood and medicants present in the blood sample without the use of specialized solid or liquid filter media. In a further aspect, this invention relates to a novel method and apparatus for diagnosing septicemia.

Septicemia, which is the presence of pathogenic microorganisms in the blood, is one of the most serious types of infection encountered. Even though modern medicine has provided an armanant of antibiotics and fungal drugs, the mortality rate from septicemia is approximately 25%. In addition, when shock accompanies septicemia, the mortality rate increases to over 60%. Dibilitating diseases, major surgery, administration of immuno suppressive drugs or anticancer medication causes the patient to be particularly prone to septicemia.

Early administration of appropriate antibiotic therapy is important in fighting septicemia. Consequently, it is imperative that the physician know as rapidly as possible, not only whether the patient has septicemia, but also the identity of the infecting microorganisms and the susceptibility of the microorganisms to antibiotic agents. Thus, proper and timely diagnosis of septicemia depends upon very rapid and efficient quantitative analysis of the patient's blood. Further, it is imperative during the quantitative analysis of the patient's blood that the blood sample not be contaminated with pathogens from the laboratory environment.

Three analytical systems have been conventionally utilized to determine the presence of microorganisms in a body fluid. These conventional systems include the liquid broth culture technique, the so-called pour plate method and the filtration method using a solid matrix filter. Each of these systems has its drawbacks, and none of the systems provide for rapid detection of microorganisms in the blood sample. Generally, the liquid broth method is not quantitative, and the pour plate method and filtration method (using a solid matrix filter) are open systems subject to external contamination, e.g., the introduction of pathogens into the culture by the laboratory atmosphere or personnel.

Recently, an improved method and apparatus has been developed for determining the presence of microbial pathogenic organisms within a sample fluid including, for example, blood. This method is disclosed in U.S. Pat. No. 3,928,139, issued Dec. 23, 1975 and entitled "DETECTION OF MICROBIAL PATHOGENS". According to this improved method, rapid and quantitative detection of microbial pathogens from a sample of body fluid is provided by employing a liquid filter medium. The sample fluid is placed on a liquid filter medium within a confined sterile zone. The liquid filter medium has a density greater than the sample fluid and comprises a sterile aqueous solution which will selectively receive microbial pathogens from the sample fluid. The confined sterile zone is thereafter subjected to centrifugation to force the sample fluid against the liquid filter medium and cause microbial pathogens to selectively pass therein and thereby separate from the mass of the body fluid sample. Next, the liquid filter medium containing the microbial pathogens is separated from the remainder of the sample fluid and portions of the liquid filter medium are subjected to various culturing conditions.

The improved method described above does provide a very rapid and efficient procedure for separating microbial pathogens from a sample fluid. According to the preferred embodiment of the liquid filter medium method, the blood sample is lysed prior to the centrifugation step which causes the microbial pathogens to be selectively received by the liquid filter medium. Other pretreating agents, such as anti-coagulating agents are also used to prepare the blood sample. Some ingredients of the preferred liquid media employed by the improved method discussed above are incompatible with some of the pretreating and/or lysing agents. Furthermore, such agents will admix with the liquid filter medium if added thereto prior to the time that the blood sample is added to the confined sterile zone, and once so admixed such agents cannot diffuse from the liquid filter medium rapidly enough to effectively treat the blood. Therefore, it is necessary either to subject the blood samples to the possibility of external contamination by admixing the blood sample with the pretreating and/or lysing agents prior to introducing the sample into a closed sterile system or to employ a specialized apparatus whereby the treating agent may be contained within the closed system but separate from the liquid filter medium until the apparatus is placed into use. Apparatus of this type are disclosed in U.S. Pat. No. 3,875,012, issued Apr. 1, 1975 and entitled "APPARATUS AND METHOD FOR THE DETECTION OF MICROBIAL PATHOGENS" and in U.S. Pat. No. 3,932,222, issued Jan. 13, 1976 and entitled "FOR ISOLATING PATHOGENIC MICROORGANISMS".

Furthermore, when using the above-described improved method for detecting microbial pathogens in blood samples, using a liquid filter medium in a centrifugation vessel which includes an injectable closure means at the end of the vessel against which the blood sample and liquid filter medium are forced by centrifugation, it has been discovered that some of the heavier microbial pathogens, which are received by the liquid filter medium, can pass, under the force imparted by centrifugation, completely through the liquid filter medium and come to rest adjacent the bottom of the centrifugation vessel being employed. Unless great care is taken during separation and recovery of the liquid filter medium some of such microbial pathogens can be left behind, unrecovered. It is believed that the loss of microbial pathogens, in such cases, occurs because upon passing completely through the liquid filter medium the microbial pathogens become lodged in the tiny crevice formed between the wall of the centrifugation vessel and the injectable closure means.

In an effort to overcome the above difficulties encountered when a liquid filter media is employed a new technique has been developed employing a high density, water immiscible, hydrophobic, nontoxic, liquid cushioning agent. This technique is disclosed in applicant's copending application Ser. No. 739,274, filed Nov. 5, 1976, and entitled "METHOD FOR DETECTING MICROBIAL PATHOGENS EMPLOY- ING A CUSHIONING AGENT". Basically this novel technique employs a liquid substance for a cushioning agent which allows microbial pathogens to collect on or in the cushioning agent, without passing through it, upon centrifugation. The use of a liquid filter media which selectively receives the microbial pathogens, and in some cases allowed some of such pathogens to pass completely therethrough, is eliminated. Basically, the liquid cushioning agent provides a means for ensuring that separated microbial pathogens are not lost or unrecovered as a result of being entrapped in crevices or interstitial spaces within the centrifugation receptacle during the centrifugation step. This method, while being highly effective does require the use of liquid cushioning agent having specified properties.

Thus, it is desirable to have a closed, sterile method for separating and concentrating microbial pathogens suspected to be present in a blood sample without the necessity of having to premix the blood sample in a potentially contaminated environment and without the necessity of employing specially designed apparatus for accomplishing the pretreating step of the procedure. Furthermore, a procedure for recovery of microbial pathogens which does not necessitate the use of specialized filter mediums or cushioning agents is especially desirable.

SUMMARY OF THE INVENTION

The method of the present invention provides for a relatively simple, yet effective means of separating microbial pathogens from a blood sample and collecting the concentrated microbial pathogens for analysis by conventional culture techniques. Basically, it has been discovered that by depositing a lysed blood sample within a confined sterile zone which comprises a continuous smooth surface microbial pathogens present in such a sample can be separated and concentrated therefrom by subjecting the confined sterile zone to centrifugation thereby causing the pathogenic microorganisms in the blood sample to gravitate toward and collect on the continuous smooth surface of the confined sterile zone. The major portion of the lysed blood sample is then removed from the confined sterile zone and the concentrated microbial pathogen may then be separately removed from the confined sterile zone for analysis. Such a procedure not only concentrates any microbial pathogens present but also separates them from antimicrobial constituents present in the blood sample.

In one embodiment of the present invention, the confined sterile zone can comprise an elongated centrifugation receptacle with a continuous smooth surface at one end thereof and an opening at the other end thereof, for example, a glass test tube. The closed end of such a receptacle provides an excellent surface upon which microbial pathogens will collect upon centrifugation of a lysed blood sample. In order to maintain a sterile environment and avoid contamination it is preferable to carry out the separation of microbial pathogens in a sterile closed environment. Accordingly, the elongated centrifugation receptacle may be sealed with an injectable closure member at the opening thereof and the air contained therein evacuated. This allows for the injection of a blood sample into the receptacle without the necessity for opening the system to the atmosphere.

In a preferred embodiment of the subject invention the blood sample is lysed within the centrifugation receptacle, thus eliminating any possible contamination of the blood which might occur during a separate lysing procedure. For example, the blood sample may be lysed within the centrifugation receptacle by injecting it through an injectable closure means and into the centrifugation receptacle which contains a predeposited portion of a suitable lysing agent. It is important to note that the lysing agent employed must be nontoxic to microbial pathogens. Thus, a blood sample may be injected directly into the centrifugation receptacle and upon agitation of the receptacle the blood sample will be lysed by the lysing agent contained therein.

It has been discovered that microbial pathogens present in a lysed blood sample can be separated therefrom by subjecting the centrifugation receptacle to centrifugal force in a manner such that microbial pathogens present in the sample are forced toward and collect adjacent a smooth continuous surface of the centrifugation receptacle. Upon centrifugation, the microbial pathogens present will collect in a button like form on the smooth continuous surface, and in this concentrated form, can be easily separated from the residual portion of the lysed blood sample. Such separation can be accomplished, for example, by inserting a needle, attached to a common type syringe, through the injectable closure means of the centrifugation receptacle and withdrawing the major portion of the residual blood sample. Preferably, the needle employed will be such that upon full injection into the centrifugation receptacle a small portion of residual blood sample and microbial pathogens, collected adjacent the continuous smooth surface, will be left behind within the centrifugation receptacle. The microbial pathogens can then be resuspended in the minor portion of residual blood sample by mixing to ensure complete recovery. The resuspended microbial pathogens can then be removed from the centrifugation receptacle in a number of ways, including employing a needle of sufficient length to reach the bottom of the centrifugation receptacle (the aperture of the tip of the stylus resting adjacent the continuous smooth surface) or, by inverting the centrifugation receptacle and employing a short stylus injected through the injectable closure means in a manner such that the aperture of the short stylus is adjacent the interior face of the injectable closure means thus providing removal of the resuspended microbial pathogens and residual blood sample. The microbial pathogens recovered in this manner may then be plated on culture media for conventional types of quantitative and qualitative analysis.

In another embodiment of the present invention, a novel article is provided for recovering microbial pathogens from a sample fluid. The novel article comprises a smooth continuous surface within a centrifugation receptacle such that on centrifugation of the centrifugation receptacle sample fluid being centrifuged will be forced against the surface at a substantially perpendicular angle. Of course, when a swinging bucket type centrifuge is utilized, the smooth continuous surface employed can simply be the hemispherical end of a common test tube. However, when a more common angle rotor centrifuge is employed centrifugal force imparted to a fluid contained in an elongated centrifugation receptacle seated in such a centrifuge will not normally be forced against a substantially perpendicular, continuous, smooth surface. For example, if a common test tube is employed in an angle rotor centrifuge the force imparted to a liquid contained therein will be in a substantially horizontal direction and therefore will contact the side wall of the test tube at the same angle at which the test tube rests within the angle centrifuge.

Thus, when an angle centrifuge is employed improved results have been obtained by fabricating a continuous smooth surface within the centrifugation receptacle disposed at an angle which is substantially the complement of the angle at which the centrifugation receptacle is to be spun. In this manner, the blood sample contained in the centrifugation receptacle, at least at the lower portions thereof, will be forced against a continuous smooth surface which is positioned at substantially a perpendicular angle with respect to the centrifugal force applied.

While an exact theory explaining the improved results when employing a continuous smooth surface disposed at an angle substantially perpendicular to that of the imparted centrifugal force cannot be set forth it is believed that improved recovery is due, in part, to the fact that such an arrangement provides a shorter path length of travel for pathogens and therefore a greater average "g" force to be imparted upon pathogens to provide a more efficient concentrated deposit thereof which can be easily removed from the centrifugation vessel. Further, the use of a centrifugation vessel which employs such a design results in an increase in centrifugation efficiency in that centrifugation can be carried out at less g's within the same time period as in conventional centrifugation, or at the same g's in a shorter time period, than the conventional procedure.

Thus, the subject invention provides a method for detecting microbial pathogens in a blood sample and separating such pathogens from the majority of the blood sample, which may contain antipathogenic constituents or medicants which would inhibit growth and analysis of the microbial pathogens. This procedure can be carried out in a completely closed system, so as to prevent possible contamination from laboratory environment, and does not require the use of any specialized liquid filter medium or cushioning agents.

DETAILED DESCRIPTION OF THE INVENTION

This invention can be more easily understood from a study of the drawings in which:

FIG. 1 is a cross-sectional view of the preferred centrifugation article of the present invention; and FIGS. 2-9 depict the steps of the improved method for detection of microbial pathogens employing the article of FIG. 1.

Now referring to FIG. 1, the preferred embodiment of the improved centrifugation article of the present invention will be described. As shown, the article 20 comprises an elongated, tubular centrifugation vessel 22 having an injectable closure member 24 which sealably closes the upper end thereof. When article 20 is to be employed in the preferred embodiment of the method of detecting microbial pathogens of the present invention, an effective amount of blood treating agents 30 can be deposited therein.

Centrifugation vessel 22 can be made of siliconized glass or hard plastic, such as polycarbonate or polypropylene. Injectable closure member 24 can comprise a rubber self-sealing stopper. Injectable closure member 24 includes indentation 24a in the top surface thereof to enhance the ease of injection by common types of medical injection needles. It is further noted that the interior surface 26 of injectable closure member 24 meets the tubular walls of centrifugation vessel 22 at substantially a perpendicular angle and is not beveled. This arrangement provides for a tight seal between the injectable closure member 24 and the walls of the centrifugation vessel 22 thereby providing against possible entrapment of microbial pathogens at the interface of the closure member and the centrifugation vessel upon inversion of the centrifugation vessel for removal of the microbial pathogens (as described in detail below). The use of a nonbeveled closure member 24 is preferred, however, conventional beveled stoppers may be employed without serious detrimental effect.

The evacuated space 32 is maintained at a lower than atmosphere pressure, at a predetermined value, so that the centrifugation vessel can receive a known amount of liquid by injection through injectable closure member 24 without excessive pressure being built up within the interior thereof which would cause injectable closure member 24 to become dislodged from the opening of centrifugation vessel 22. It is noted that article 20 is especially designed to be utilized within an angle rotor centrifuge and that the angle of surface 34, at the bottom of centrifugation vessel 22 is substantially the complement of the angle of the rotor, with respect to a horizontal plane. It is noted that if the device of the subject invention is utilized in a conventional swinging bucket type centrifuge the rounded bottom of centrifugation vessel 22 could be employed as the smooth continuous surface against which centrifugal force is imparted, or a substantially flat horizontal bottom surface, positioned at a substantially right angle with the walls of the centrifugation vessel 22 could be employed. In any case, smooth continuous surface 34 should be substantially free of interstitial spaces and crevices in which microbial pathogens could become entrapped. Further, the circular sealing area around surface 34, where the material employed to form the surface meets the walls of centrifugation vessel 22, should be tightly sealed so that the interface does not provide a large circular crevice in which microbial pathogens could become lodged.

Generally, rotor angles in rotor centrifuges range from about 60 degrees to 10 degrees and therefore the angle of surface 34, or angle of incline 36 within the centrifugation vessel will range correspondingly from 30 degrees to 80 degrees. Thus, the angle of incline, depicted by arc 36, will generally be the complement of the angle at which article 20 rests within the centrifuge during centrifugation. For example, the angle of incline 36 depicted in FIG. 1 is approximately 34 degrees. Thus, for example, when article 20 is placed in an angle rotor centrifuge in which centrifugation occurs at approximately 56 degrees, fluids contained within article 20 will be forced against surface 34 at a substantially perpendicular angle.

When employing a common type test tube as centrifugation vessel 22 surface 34 can be provided by employing a plug 38 of material adjacent the bottom of the centrifugation article, as depicted in FIG. 1. Such a plug 38 can be manufactured from any of a number of materials which provide a smooth surface, a good seal with the wall of centrifugation vessel 22, and which are nontoxic to microbial pathogens. One method of fabricating such a plug is to do so in situ by employing a material which can be poured into centrifugation vessel 22 and allowed to set therein. The material should be fluid enough and have setting times long enough to allow centrifugation vessel 22 to be placed at the desired angle of incline with the result that the material flows to the desired angle of incline and then sets. Upon setting, the material will provide a smooth surface 34 and a good seal with the walls of centrifugation vessel 22. Examples of such materials are common bathtub caulks and silicone based resins which are provided in a low viscosity liquid form and which cure to form an elastomeric material. An example of the latter type of material is a silicone based fluid resin sold under the trade name "SYLGARD 134" by Dow Corning, Midland, Mich. When a material such as SYLGARD is employed, it is sometimes advisable to use a primer on the interior wall of centrifugation vessel 22 in order to ensure a good seal between the cured SYLGARD and the centrifugation vessel wall 22. A suitable primer is sold under the trade name "DC 1200" by Dow Corning. Thus, for example, a smooth inclined surface 34 which is depicted in FIG. 1, can be prepared by priming the interior wall of centrifugation vessel 22 with a suitable silicon base resin primer such as DC 1200, and pouring an amount of a liquid silicon based resin such as SYLGARD 134 into centrifugation vessel 22, placing the entire vessel at the desired angle of incline and curing the silicone resin under appropriate conditions to form an elastomeric plug having a smooth surface 34 positioned at the desired angle of incline within centrifugation vessel 22. Bathtub caulking and similar materials may be employed in the same general manner, if desired, and the correct angle of incline may be formed by centrifuging the article containing the uncured plug forming material in the type of centrifuge with which the article is to be employed.

After smooth continuous surface 34 has been prepared in one of the above described manners, treating agents which can include, for example, lysing agents and/or anti-coagulants can be deposited within centrifugation vessel 22 prior to evacuation and sealing thereof with injectable closure means 24. Any suitable lysing agent can be utilized so long as it is nontoxic to microorganisms. A suitable such lysing agent is an aqueous solution of a nontoxic saponin. It must be noted that many saponins are known to be toxic to microbial pathogens. However, as set forth in applicant's U.S. Pat. No. 3,883,425, issued May 13, 1975, and entitled "DETOXIFICATION OF SAPONINS", which is herein incorporated by reference, a method is disclosed for removing the toxic ingredients from the heretofore thought to be toxic saponins. In general, the toxic saponin material can be detoxified in accordance with the invention set forth in that patent and the resulting purified material used within the scope of this invention. In addition, the aqueous solution of saponin can contain an anti-coagulant and/or oxygen scavenger. A preferred anti-coagulant is sodium polyanethol sulfonate (SPS) or heparin, for example. Sodium polyanethol sulfonate is preferred because it not only acts as an anti-coagulant but also inhibits the phagocytic activity of granulocytes and monocytes and the normal antibacterial activity of blood serum. It is preferred that said aqueous solution of treating agents be at least 1.0% by volume of the total liquid in centrifugation vessel 22 (including the treating solution and sample fluid) and preferably from about 7.6% to about 17.5% by volume thereof.

Once the treating agents 30 have been deposited in centrifugation article 20, injectable closure member 24 can be put in place and space 32 evacuated to a desired lower than atmospheric pressure.

Now referring to FIGS. 2-9 an analysis sequence is schematically depicted illustrating a preferred embodiment of the preferred invention. As an example, a procedure which is carried out in accordance with one embodiment of this invention for detection of microbial pathogens within a blood sample can be carried out conveniently with the following apparatus:

The above-described centrifugation article 20 contains the blood treating agents 30–the vessel can be of 12-14 millimeters in volume.

A sterile glass syringe and one 3¼ inch 16 gauge spinal tap disposable needle;

one sterile glass syringe and one relatively short needle substantially equal in length to the thickness of injectable closure member 24;

one ⅝ inch 25 gauge hypodermic needle with cotton inserted in its hub (used as a vent);

three blood agar plates;

one chocolate agar plate;

one Sabouraud plate.

It is noted that with the exception of centrifugation article 20, or some equivalent article, and perhaps the shorter needle employed with this embodiment of the present invention, various types of well known laboratory apparatus and culture media can be used to carry out the novel process of the subject invention. It is particularly noted that the culture media set forth above are exemplary only and are generally preferred to be utilized for detecting the most commonly known microbial pathogens. The blood agar plates suggested are conventionally utilized blood agar plates which are basically sheep's blood and a base nutritional agent such as sugar, which is held together with an agar solidifying agent on a Petri plate. The chocolate agar plate is designed to grow certain fastidious pathogens, e.g., hemophilus. The Sabouraud plate is specifically designed to grow fungi.

Thus, while various apparatus can be utilized in the method of the subject invention, the above-listed apparatus and materials can be conveniently utilized in the scope of this invention in a manner set forth below.

To utilize centrifugation article 20, as set forth in FIG. 1 of the drawings, it is initially positioned so that injectable closure member 24 is at the upper end thereof and the blood treating fluids 30 rest upon smooth continuous angled surface 34. Next, a predetermined amount of blood sample 39 drawn from the patient, for example, 8 milliliters of blood, is injected into the evacuated space of centrifugation article 20, as depicted in FIG. 3, using a common type of syringe 40. Alternatively, the sample can be drawn directly into article 20 using a standard double needle fixture supplied with conventional vacuum blood drawing devices such as are sold under the mark "VACUTAINER" by Beckten Dickenson. Then, article 20 containing the blood sample 39, and the blood treating fluid 30 is subjected to mixing to ensure that the blood treating agents 30 are completely admixed with the blood sample 39. This mixing step is depicted schematically in FIG. 4.

After the blood sample 39 has been treated in this manner, centrifugation article 20 is centrifugated to cause the microbial pathogens within the treated blood sample 42 to pass out of suspension and collect adjacent continuous smooth surface 34. Some microbial pathogens will actually be deposited upon the side wall of centrifugation vessel 22 adjacent the high end of smooth surface 34 at point 22a. This centrifugation step is represented schematically by FIG. 5. The speed and time of centrifugation can vary widely depending upon the construction material of centrifugation article 20 and the type of centrifugation apparatus. The centrifugation can be conveniently accomplished by imparting from between about 1500 and 6000 gravities and preferably from about 1500 to 3000 gravities to the centrifugation article 20 containing the treated blood sample 42. As depicted in FIG. 5, an angle rotor centrifuge is employed which places the centrifugation article 20 at an angle of 56 degrees, for example, (depicted by arc 44) during centrifugation. Thus, if smooth angled surface 34 is at a 34 degree angle with respect to the interior walls of the centrifugation article 20, the treated blood sample 42 will be forced against smooth angled surface 34 at a relatively perpendicular angle during centrifugation. It is noted that when a swinging bucket type of centrifuge is employed, centrifugation article 20 will be centrifuged at substantially zero degrees with respect to a horizontal surface. Thus, in such a case, the angle of surface 34 will be approximately 90 degrees with respect to the walls of centrifugation article 20, or can be the rounded bottom surface of a conventional test tube.

Once the centrifugation step has been completed, centrifugation article 20 can be removed from the centrifuge and the major portion of the treated blood sample 42 from which microbial pathogens have been separated can be removed. It is noted that, as used herein, the term "residual treated blood" or "residual blood" refers to a blood sample which has been centrifuged such that the microbial pathogens present therein have collected at the bottom of the sample, hence, leaving the "residual" portion of the sample substantially free of microbial pathogens. This step is depicted in FIG. 6. To aid in ease of removal, a vent needle 46 in the form of a common hypodermic needle with cotton in its hub, for example, is injected through injectable closure member 24. A second hypodermic needle with syringe 45 attached can be injected through injectable closure member 24 to remove a major portion of the residual treated blood sample 42 from which microbial pathogens have been separated. For example, when a centrifugation vessel has a volume of from 12 to about 24 millileters, a 3½ inch 16 gauge spinal tap needle can be inserted through the injectable closure member 24 to remove all but about 1 millileter of the treated blood sample 42. As shown, it is preferred that the major portion of residual blood samples be withdrawn from the interior of centrifugation vessel 22 at a point opposite the side wall adjacent the upper end of smooth surface 34 to avoid disturbing the layer of microbial pathogens which has formed on the side wall of centrifugation vessel 22 adjacent the upper end of said smooth surface 34. The majority of the residual blood sample is removed in this step, however, a small portion of the residual blood sample should be left in the centrifugation vessel 22.

Once the major portion of the treated residual blood sample has been removed, both needles may be withdrawn from injectable closure member 24 and centrifugation article 20 is then subjected to a second mixing step depicted schematically by FIG. 7. The second mixing step serves to resuspend microbial pathogens which have been separated from the major portion of residual treated blood sample 42 and which have formed in a button like layer on smooth surface 34. Resuspension of the microbial pathogens so collected in the remaining minor portion of the residual treated blood sample 42 ensures greater and more uniform recovery as well as providing good separation of the microbial pathogens within the minor portion of the residual treated blood sample 42.

Once the mixing step has resuspended the microbial pathogens in a minor portion of the residual treated blood sample 42, the mixture of microbial pathogens and residual treated blood sample can be removed from centrifugation article 20. This step can be accomplished in a variety of ways, including the method depicted in FIG. 8. As shown in FIG. 8, centrifugation article 20 can be inverted so that the mixture of the minor portion of residual blood sample and microbial pathogens rests on top of injectable closure member 24. Then, a shortened stylus affixed to a common syringe 50 can be inserted through injectable closure member 24 such that the aperture at the tip of the stylus communicates with the interior of centrifugation article 20 at a point near the inner surface 26 of injectable closure member 24. The residual portion of the treated blood sample, and microbial pathogens suspended therein, may then be removed with the syringe. Alternately, centrifugation article 20 may remain in an upright position and a needle of sufficient length to reach the lower end of angled smooth surface 34 can be injected through injectable closure member 24 and the microbial pathogen-residual blood sample mixture can be withdrawn in this manner. It is also within the scope of the present invention to merely remove injectable closure member 24 from the opening of centrifugation article 20 and remove the resuspended microbial pathogens by pipette or other means. However, such procedures do present an opportunity for contamination to occur.

Once the mixture of microbial pathogens and minor portion of residual blood sample has been removed from article 20 it can be deposited on bacterial growth media. This step is schematically illustrated in FIG. 9 of the drawings. With the apparatus set forth above, the material can be distributed as follows:

One blood agar plate can receive 0.2 milliliters and the plate can be incubated at 36 degrees C. in an aerobic atmosphere. Two blood agar plates can receive 0.2 milliliters of the aqueous solution and can be incubated at 36 degrees C. in an anaerobic environment. One chocolate agar plate can receive 0.2 milliliters of the aqueous solution and can be incubated at 36 degrees C. in a candle jar. The Sabouraud plate can receive 0.2 milliliters of the mixture and can be incubated at 25 degrees C. in an aerobic environment. The growth media should be checked daily for the presence of colonies. Microscopic analysis techniques can for employed. The number of microbial pathogens in one milliliter of the blood can be determined by multiplying the number of colonies by a correction factor. This correction factor takes into consideration the recovery rate for a given organism, the volumes of blood employed and the amount of final mixture plated. In the example set forth above, the correction factor is 0.13.

It should again be noted that the exact procedural steps, apparatus, equipment and types of culture media utilized in the detailed embodiment set forth above can vary, as desired. For example, any known means can be utilized to admix the blood sample with the anti-coagulant and/or lysing agent. Various other modifications can be used in the procedure as desired.

EXAMPLE

The following example is given to better facilitate the understanding of this invention and is not intended to limit the scope thereof.

The process of the subject invention was used in the test recovery of four different types of microbial pathogens. In each case, a centrifugation article, in the shape of a conventional test tube with a rubber stopper, sold under the trade name "VACUTAINER" Number 4710 by Beckten Dickenson & Co., Cockeysville, Md. was employed. To each of these centrifugation articles was added 0.3 ml. of saponin and 0.1 ml. of a 5% solution of sodium polyanethol sulfonate (SPS) made by Hoffmann-La Roche Inc., Nutley, N.J. These articles were then sterilized by autoclaving at 121 degrees C. for 15 minutes. For each different organism tested, 8 ml. of whole blood (admixed with an anti-coagulant, CPD contained in blood bags sold by Fenwal Laboratories, a division of Travenol Laboratories, Inc., Deerfield, Ill. was placed in each tube with a sterile syringe and needle. A bacterial suspension containing approximately 1000 cells was introduced into the system, the inoculum having a volume of approximately 0.1 ml.

Each centrifugation article was thoroughly mixed, by agitation, thereby lysing the whole human blood. After the mixing step, each of the centrifugation articles was centrifuged in an RC5 centrifuge sold by E. I. duPont de Nemours and Company, Wilmington, Del., using an SS-34 angle rotor at 3000 RCF for approximately 30 minutes. In each case a button-like layer of microbial pathogens was observed to collect at the glass surface at the bottom of the article.

After centrifugation, a 2½ inch 16 gauge spinal tap needle was inserted through the stopper towards the bottom of the centrifugation article. This needle was the proper length for removing the major portion of the treated blood sample and leaving approximately 1 ml. behind. A vent in the form of a ⅝ inch 25 gauge needle, with cotton in its hub was inserted through the stopper and the residual treated blood sample, in the amount of approximately 8 ml., was slowly withdrawn. All needles were then removed from the stopper and the remaining portion of the residual blood sample and the microbial pathogens were subjected to a second mixing step which resulted in resuspension of the microbial pathogens in the minor remaining portion of the treated blood sample. The rubber stopper of the centrifugation article was then removed and a 1 ml. sterile pipette was used to draw out the resuspended microbial pathogens. This mixture of microbial pathogens and residual portion of the treated blood sample was evenly distributed on five nutrient agar plates.

After a 24 hr. period the number of colonies on each plate were counted and recovery rate determined. The recovery rate for each organism tested is set forth in Table 1.

TABLE 1

| ORGANISM | RECOVERY RATE |
| --- | --- |
| Escherichia Coli | 86 ± 2 |
| Escherichia Coli | 88 ± 6 |
| Staph Aureus | 87 ± 5 |
| Pseudomonas | 91 ± 2 |
| Candida Albicans | 95 ± 1 |

While this invention has been described in relation to its preferred embodiments, it is to be understood that various modifications thereof will now be apparent to one skilled in the art upon reading the specification and it is intended to cover such modifications as fall within the scope of the appended claims.

What is claimed is:

1. In a method of detecting the presence of microbial pathogens in a lysed blood sample wherein blood is mixed with a lysing reagent, the improvement consisting of:

concentrating said microbial pathogens and separating said microbial pathogens from the residual of said lysed blood sample by;

depositing said lysed blood sample on a continuous smooth surface within a confined sterile zone;

subjecting said confined sterile zone containing said lysed blood sample to centrifugation thereby causing said microbial pathogens to pass out of suspension in said lysed blood sample and concentrate on said continuous smooth surface; and separating said concentrated microbial pathogens from contact with the residual portion of said lysed blood sample.

2. The method of claim 1 wherein said continuous smooth surface is positioned within said confined sterile zone in a manner such that upon centrifugation, said continuous smooth surface lies in a plane substantially perpendicular to the centrifugal force imparted thereto.

3. In a method of detecting the presence of microbial pathogens in a blood sample which is suspected to contain said microbial pathogens and antipathogenic factors wherein blood is mixed with a lysing reagent, the improvement consisting of:

depositing said blood sample in a confined sterile zone on a continuous smooth surface therewithin, said confined zone containing an effective amount of a lysing agent to lyse said blood sample;

subjecting said confined sterile zone containing the lysed blood sample to centrifugation for a time sufficient to cause said microbial pathogens to pass out of suspension in said lysed blood sample and concentrate on said continuous smooth surface; and separating said concentrated microbial pathogens from the residual of said lysed blood sample.

4. The method of claim 3 wherein said continuous smooth surface is positioned within said confined sterile zone in a manner such that upon centrifugation, said continuous smooth surface is substantially perpendicular to the direction in which said blood sample is forced.

5. The method of claim 3 and further comprising resuspending said concentrated microbial pathogens in a portion of said residual blood sample and thereafter quantitatively plating the admixed body on growth media for microbial pathogens.

6. The method of claim 5 and further comprising microscopically analyzing said mixture of microbial pathogens and residual blood sample.

7. A method of detecting microbial pathogens in a blood sample which is lysed by mixing a lysing reagent therewith and wherein said sample is suspected to contain suspended microbial pathogens and antipathogenic factors consisting of:

depositing said lysed blood sample on a smooth continuous surface in an evacuated centrifugation tube;

subjecting said centrifugation tube containing said lysed blood sample to centrifugation in a manner to force said blood sample against said continuous smooth surface and cause substantially all of said microbial pathogens to pass out of suspension and collect in a layer on said continuous smooth surface;

separating a major portion of the residual blood sample from said layer of microbial pathogens;

admixing said layer of microbial pathogens with a remaining minor portion of said residual blood sample;

removing the resulting mixture from said centrifugation tube; and analyzing the resultant mixture for the presence of microbial pathogens.

8. The method of claim 7 wherein said blood sample is lysed within said centrifugation tube.

9. The method of claim 7 wherein said continuous smooth surface is positioned such that upon centrifugation, said blood sample will be forced against said surface at a substantially perpendicular angle.

10. The method of claim 7 wherein said resultant mixture is analyzed by a method comprising plating said resultant mixture on growth media for said microbial pathogens.

* * * * *

UNITED STATES PATENT AND TRADEMARK OFFICE
CERTIFICATE OF CORRECTION

PATENT NO. : 4,164,449
DATED : August 14, 1979
INVENTOR(S) : Gordon L. Dorn, et al.

It is certified that error appears in the above-identified patent and that said Letters Patent are hereby corrected as shown below:

Column 8, line 6, change "3-1/4" to --3-1/2--.
       line 56, change "centrifugated" to --centrifuged--.
Column 10, line 44, change "for" to --be--.
Column 11, line 10, change "Ill." to --Ill.)--.

Signed and Sealed this

Fourth Day of December 1979

[SEAL]

Attest:

SIDNEY A. DIAMOND

Attesting Officer      Commissioner of Patents and Trademarks